(12) United States Patent
Kwak et al.

(10) Patent No.: US 10,968,346 B2
(45) Date of Patent: Apr. 6, 2021

(54) METHOD OF MANUFACTURING NANOSTRUCTURE WITH IMPROVED CELL ADHESIVE ABILITY CONTAINING FUCOIDAN AND NANOSTRUCTURE WITH IMPROVED CELL ADHESIVE ABILITY CONTAINING FUCOIDAN MANUFACTURED THEREBY

(71) Applicant: AJOU UNIVERSITY INDUSTRY-ACADEMIC COOPERATION FOUNDATION, Suwon-si (KR)

(72) Inventors: Jong Young Kwak, Suwon-si (KR); Jung Min Kim, Jinju-si (KR); Yeo Jin Park, Bucheon-si (KR); Dan Bi Park, Seongnam-si (KR); Young Hun Jeong, Daegu (KR); Jeong Hwa Kim, Yongin-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 111 days.

(21) Appl. No.: 16/299,835

(22) Filed: Mar. 12, 2019

(65) Prior Publication Data
US 2019/0270883 A1 Sep. 5, 2019

Related U.S. Application Data

(63) Continuation-in-part of application No. PCT/KR2017/009135, filed on Aug. 22, 2017.

(30) Foreign Application Priority Data

Sep. 13, 2016 (KR) .................. 10-2016-0118410

(51) Int. Cl.
*C08L 67/04* (2006.01)
*A61L 27/46* (2006.01)
(Continued)

(52) U.S. Cl.
CPC .............. *C08L 67/04* (2013.01); *A61L 27/18* (2013.01); *A61L 27/46* (2013.01); *A61L 27/50* (2013.01);
(Continued)

(58) Field of Classification Search
CPC ........ D01D 5/0061; D01D 5/003; D01D 1/02; D01D 5/0007; D01F 1/10; D01F 6/625;
(Continued)

(56) References Cited

FOREIGN PATENT DOCUMENTS

| CN | 104436205 A | 3/2015 |
|---|---|---|
| KR | 10-1684698 B1 | 12/2016 |

OTHER PUBLICATIONS

Ferreira et al. Electrospinning Polycaprolactone Dissolved in Glacial Acetic Acid: Fiber Production, Nonwoven Characterization, and In Vitro Evaluation. Journal of Applied Polymer Science (2014), 131, 9 pages. (Year: 2014).*

(Continued)

*Primary Examiner* — Sean C. Barron
(74) *Attorney, Agent, or Firm* — Sughrue Mion, PLLC

(57) ABSTRACT

The present invention relates to a method of manufacturing a polycaprolactone nanostructure with improved cell adhesive ability containing fucoidan according to the present invention comprises dissolving fucoidan in glacial acetic acid as a solvent to obtain fucoidan-glacial acetic acid solution, mixing polycaprolactone with the fucoidan-glacial acetic acid solution to obtain a polycaprolactone-mixed solution, and manufacturing a nanostructure from the polycaprolactone-mixed solution by an electrospinning method. Therefore, a polycaprolactone nanostructure with improved (Continued)

cell adhesive ability containing fucoidan manufactured by the method according to the present invention exhibits characteristics of preventing fucoidan from being released from nanofibers by uniformly distributing fucoidan in the polycaprolactone nanostructure. Accordingly, the fucoidan-containing polycaprolactone nanostructure exhibits an effect capable of controlling cell activity while culturing adhered cells by facilitating adhesion of various types of cells.

4 Claims, 11 Drawing Sheets

(51) Int. Cl.
| | | |
|---|---|---|
| C12N 5/00 | (2006.01) | |
| D01D 5/00 | (2006.01) | |
| A61L 27/18 | (2006.01) | |
| A61L 27/54 | (2006.01) | |
| A61L 27/50 | (2006.01) | |
| C08J 3/07 | (2006.01) | |
| B82Y 30/00 | (2011.01) | |

(52) U.S. Cl.
CPC ............... *A61L 27/54* (2013.01); *C08J 3/07* (2013.01); *C12N 5/0062* (2013.01); *C12N 5/0068* (2013.01); *D01D 5/0007* (2013.01); *D01D 5/0061* (2013.01); *A61L 2300/232* (2013.01); *A61L 2400/12* (2013.01); *B82Y 30/00* (2013.01); *C12N 2533/30* (2013.01)

(58) Field of Classification Search
CPC .......... A61L 27/18; A61L 27/50; A61L 27/54; A61L 27/46; A61L 2400/12; A61L 2300/232; C08J 3/07; C12N 5/0068; C12N 5/0062; C12N 2533/70; C12N 2533/90; C12N 2533/30; C08L 67/04; B82Y 30/00

See application file for complete search history.

(56) References Cited

OTHER PUBLICATIONS

Ramazani et al. Investigating the influence of temperature on electrospinning of polycaprolactone solutions. e-Polymers (2014), 14(5), 323-333. (Year: 2014).*
Ji Seok Lee, et al., "Fabrication of electrospun biocomposites comprising polycaprolactone/fucoidan for tissue regeneration", Carbohydrate Polymers, 2012, pp. 181-188, vol. 90.
Sang-Myung Jung, et al., "Controlled activity of mouse astrocytes on electrospun PCL nanofiber containing polysaccharides from brown seaweed", In Vitro Cellular & Developmental Biology, Animal, 2012, pp. 633-640, vol. 48.
Stefanos Kikionis, et al., "Electrospun biocomposite nanofibers of ulvan/PCL and ulvan/PEO", Journal Applied Polymer Science, 2015, pp. 1-5, vol. 132, document No. 42153.
International Search Report for PCT/KR2017/009135 filed Dec. 4, 2017 [PCT/ISA/210].

* cited by examiner

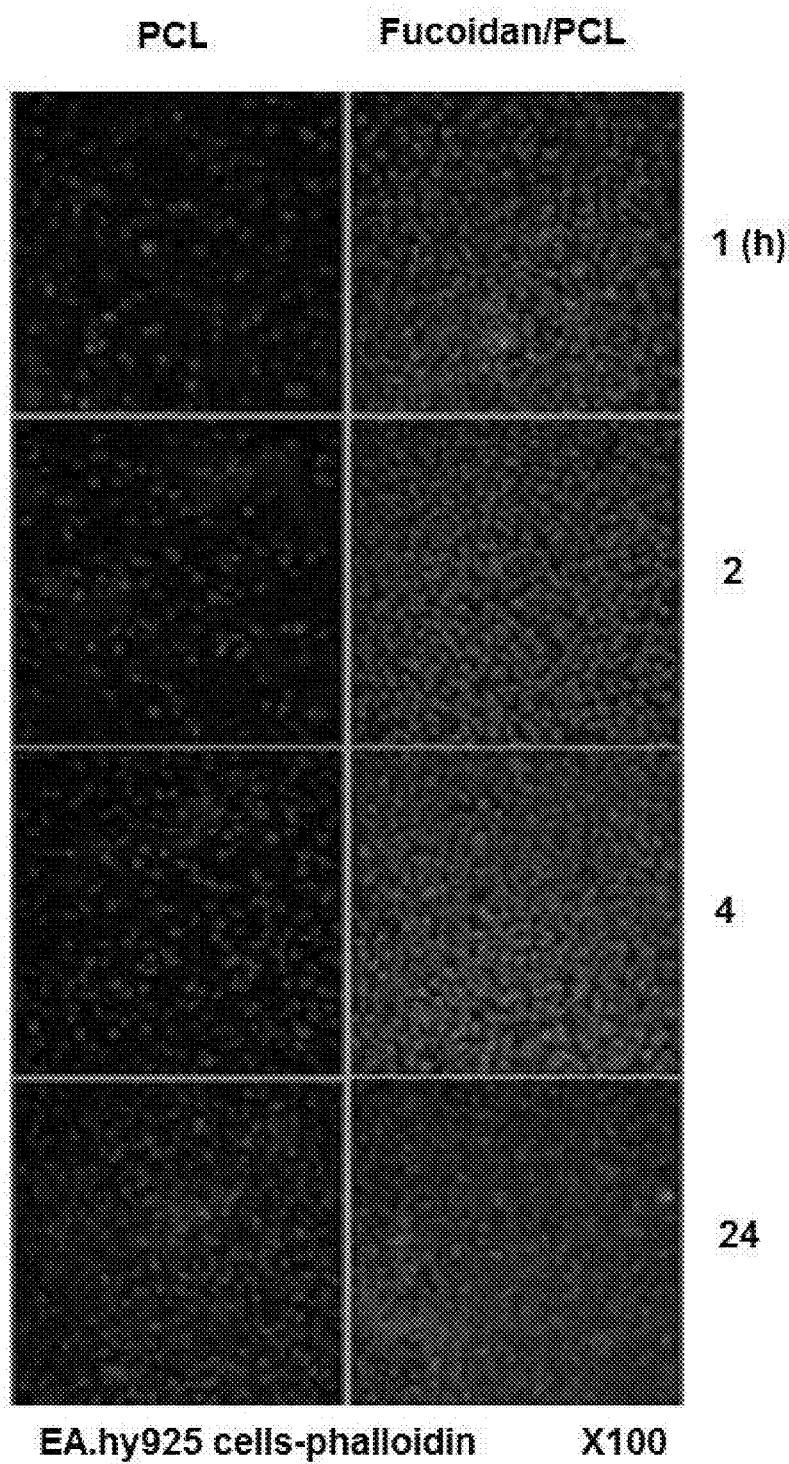

Filter paper

Fucoidan/PCL nanofiber

METHOD OF MANUFACTURING NANOSTRUCTURE WITH IMPROVED CELL ADHESIVE ABILITY CONTAINING FUCOIDAN AND NANOSTRUCTURE WITH IMPROVED CELL ADHESIVE ABILITY CONTAINING FUCOIDAN MANUFACTURED THEREBY

BACKGROUND OF THE INVENTION

Field of the Invention

The present invention relates to a method of manufacturing a polycaprolactone (PCL) nanostructure with improved cell adhesive ability containing fucoidan and a PCL nanostructure manufactured thereby, the PCL nanostructure which uniformly contains fucoidan, and has improved cell adhesive ability as fucoidan in the PCL nanostructure is not released from an aqueous solution.

Related Art

A three-dimensional cell culturing method has a very important meaning to solve problems in two-dimensional cell culture. The three-dimensional cell culturing method, as a simple method which has been attempted to create a biological tissue-mimicking cell culture environment, cultures cells using a porous biocompatible scaffold made of a nanofiber material.

Nanofibers have a large surface area in a small space, have strong durability, are very simply handled, and can be manufactured in various forms. The nanofibers have characteristics of showing a difference in pores and fiber diameters according to characteristics of synthetic polymers. The synthetic polymers which are commonly used as the nanofiber material include polyglycolic acid (PGA), PCL, and polylactic acid (PLA), and natural polymers which are commonly used as the nanofiber material include chitosan, collagen, and the like.

A nanofiber structure is suitably used in a medical field since the nanofiber structure not only has a feature of facilitating chemical bonding of various materials, but also can be manufactured using a biocompatible material. Another advantages of the nanofiber structure are that the nanofiber structure contains drugs capable of inducing or controlling activity, migration or the like of cells in three-dimensional cell culture, and enables conditions capable of slowly releasing these drugs to be made. Such an environment becomes a basic technique of measuring activities or interactions of immune cells and skin cells without drug administration in three-dimensional cell culture, and enabling the nanofiber structure to be manufactured into a nanofiber mat for transplantation. A nanofiber structure loaded with active materials may be utilized for controlling adhesion, proliferation, differentiation, and migration of cells. Therefore, developing a bioactive support having function of adhesion, viability, proliferation, differentiation or the like with respect to the cells has a very important meaning.

Although PCL is a polymer which is commonly used as material for manufacturing the nanofiber structure by an electrospinning method, a PCL nanofiber has a disadvantage of low cell adhesive ability due to hydrophobic properties. Examples of a solvent used as a PCL solution may include chloroform, acetone, methylene chloride, hexafluoropropanol, dimethylformamide, and the like. Ferreira et al. manufactured a PCL nanofiber mat using an acetic acid solution (Ferreira et al., J Appl Polym Sci. 2014; 131(22):41068). Therefore, a manufacturing technology of uniformly loading a hydrophilic material on the PCL nanofiber with hydrophobic properties is required.

Fucoidan is a polysaccharide having anions consisted of fucose and sulfate. This material has low cytotoxicity and exhibits various actions in the cells. Fucoidan increases the formation of a tube such as a blood vessel consisted of endothelial cells by binding with a fibroblast growth factor (FGF)-1 or FGF-2 that is a heparin binding protein and increasing activities thereof. When treating fucoidan in a culture of fibroblasts or myocytes, fucoidan increases production of fibrous collagens, has excellent stability with respect to the skin, and has inhibiting effects on proliferation of *E. coli*, *S. aureus*, and *C. albicans*. Fucoidan may inhibit coupling between endothelial cells and leukocytes by having an excellent binding ability with selectin which is a membrane receptor of leukocytes, platelets, and endothelial cells.

Fucoidan is a polymer having a molecular weight of about 200 kDa or more as an ingredient contained in marine algae such as kelp and sea mustard, wherein complex polysaccharides of various macromolecules including fucoidan and the like are mixed in the materials which isolating materials from the marine algae. Fucoidan which is actually commercially available is not a pure ingredient, but is a mixture of various extracted materials, and has a disadvantage that concentration of fucoidan contained in the mixture is not clear.

Although there has been an attempt of manufacturing a fucoidan-containing nanofiber to obtain a manufactured nanofiber, there has been a problem that an extract was released from the manufactured nanofiber after immersing the manufactured nanofiber into a culture medium for several hours. In order to solve the problem, techniques for loading control material by various methods such as blending with a polymer solution, or others have been developed. Lee et al. manufactured a fucoidan-containing nanofiber using electrospinning after dissolving PCL and a fucoidan powder into a mixed solution containing methylene chloride and dimethylformamide at a ratio of 8:2 (Lee et al., Carbohydr Polym. 2012; 90(1):181-8). Jung et al. reported that a PCL nanofiber manufactured by mixing a fucoidan-containing marine extract in the form of a powder together with PCL into a mixture containing tetrahydrofuran and dimethylformamide at a ratio of 7:3, has an effect on activity of astrocyte (Jung et al., In Vitro Cell Dev Biol Anim. 2012; 48(10):633-40).

However, there has been a problem that fucoidan which is hydrophilic and PCL which is hydrophobic are not substantially mixed in the form of a homogeneous mixture in nanofibers, and fucoidan is detected in the form of granules on the surface of the nanofibers.

SUMMARY OF THE INVENTION

In order to solve problems of the prior art, an objective of the present invention is to provide a new manufacturing method enabling fucoidan to be uniformly mixed with a nanofiber structure by uniformly dissolving fucoidan.

Further, the other objective of the present invention is to provide a nanofiber structure for a cell culture containing fucoidan manufactured by the manufacturing method of the present invention.

To achieve the above-described objectives, the present invention provides a method of manufacturing a PCL nanostructure with improved cell adhesive ability containing fucoidan, the method comprising the steps of: dissolving fucoidan in distilled water to obtain fucoidan-dissolved distilled water, and mixing the fucoidan-dissolved distilled water with a glacial acetic acid solution to obtain a fucoidan-glacial acetic acid solution; dissolving PCL in the fucoidan-glacial acetic acid solution to obtain a solution; stirring the solution at a temperature of 35 to 40° C. for 12 hours to obtain a resulting solution; and manufacturing a nanostructure from the resulting solution by an electrospinning method.

The method of manufacturing a PCL nanostructure with improved cell adhesive ability containing fucoidan according to the present invention comprises firstly dissolving fucoidan in distilled water to prepare the fucoidan-dissolved distilled water, and mixing the fucoidan-dissolved distilled water with a glacial acetic acid solution to fully dissolve fucoidan. In the method of manufacturing a PCL nanostructure with improved cell adhesive ability containing fucoidan according to the present invention, the step of dissolving PCL in the fucoidan-glacial acetic acid solution comprises dissolving PCL in the fucoidan-glacial acetic acid solution such that the solution has a fucoidan concentration of 0.5 to 1 mg/ml.

In the method of manufacturing a PCL nanostructure with improved cell adhesive ability containing fucoidan according to the present invention, the step of manufacturing a nanostructure from the resulting solution by an electrospinning method comprises manufacturing a nanostructure at a voltage of 8 to 10 KV and a spinning speed of 8 to 10 $\mu\ell$/min.

Furthermore, the present invention provides a PCL nanostructure with improved cell adhesive ability containing fucoidan manufactured according to the method of the present invention.

A method of manufacturing a PCL nanostructure with improved cell adhesive ability containing fucoidan according to the present invention comprises dissolving fucoidan in glacial acetic acid as a solvent to obtain fucoidan-glacial acetic acid solution and manufacturing a nanostructure from the fucoidan-glacial acetic acid solution by an electrospinning method, and a PCL nanostructure with improved cell adhesive ability containing fucoidan manufactured the above-described method according to the present invention has characteristics of preventing fucoidan from being released from nanofibers by uniformly distributing fucoidan in the PCL nanostructure. Therefore, the fucoidan-containing PCL nanostructure exhibits an effect capable of controlling cell activity while culturing adhered cells by facilitating adhesion of various types of cells.

BRIEF DESCRIPTION OF THE DRAWINGS

FIG. 2A and FIG. 2B illustrate results of experimenting if there is a difference between degree of adhesion of EA.hy926 human endothelial cells to a fucoidan-containing PCL (hereafter, fucoidan/PCL) nanofiber manufactured by Example of the present invention and degree of adhesion of the endothelial cells to a PCL nanofiber as Comparative Example.

DESCRIPTION OF EXEMPLARY EMBODIMENTS

A 15% PCL solution (5 ml) was electrospun in a 10 KV state using a 25 G metal injector under optimal conditions of a spinning speed of 8 $\mu\ell$/min and a spinning distance of 20 cm. It was shown that a remarkably large number of the endothelial cells are uniformly adhered to the entire surface fucoidan/PCL nanofiber mat manufactured by Example of the present invention compared to the PCL nanofiber mat that is Comparative Example from one hour after performing a culturing process. It was shown that more macrophages and neutrophils adhered to the entire surface of the fucoidan/PCL nanofiber manufactured by Example of the present invention in a shorter period of time than the PCL nanofiber of Comparative Example after performing a top-seeding process.

Hereinafter, preferred embodiments of the present invention will be described in more detail. However, the present invention should not be constructed as limited to the embodiments set forth herein.

<Example 1> Preparing a Fucoidan/PCL Electrospinning Solution

PCL (Mw=80.000, Sigma) and fucoidan (Fucose vesiculosus fucoidan, Mw=68.6K, sulfate 26.6% Sigma) were used, and a glacial acetic acid (Sigma) was used as a solvent.

After dissolving 50 mg/ml (w/v) or 25 mg/ml of fucoidan in distilled water to prepare 100 μℓ of a fucoidan-dissolved distilled water, and mixing the fucoidan-dissolved distilled water with 5 ml of glacial acetic acid to obtain a fucoidan-glacial acetic acid solution, PCL was added to the fucoidan-glacial acetic acid solution at a ratio of 15% (w/v) to dissolve PCL in the mixed solution at 37° C. for 12 hours.

As a Comparative Example, after dissolving 15% PCL in chloroform (Sigma) as a solvent to prepare a 15% PCL solution, 1 mg/ml (w/v) of fucoidan was dissolved in the 15% PCL solution.

<Example 2> Manufacturing a Fucoidan/PCL Nanofiber by an Electrospinning Method

A nanofiber was manufactured by controlling conditions of an electrospinning machinery using an electrospinning method, wherein the nanofiber was manufactured by performing an electrospinning process under various conditions including a PCL concentration of 10 to 15%, a voltage of 8 to 10 KV, and a spinning speed of 8 to 10 μl/min thereby, electrospinning a 15% PCL solution (5 ml) in a 10 KV state using a 25 G metal injector under optimal conditions of a spinning speed of 8 μl/min and a spinning distance of 20 cm.

<Experimental Example> Measuring SEM

Figure 1:
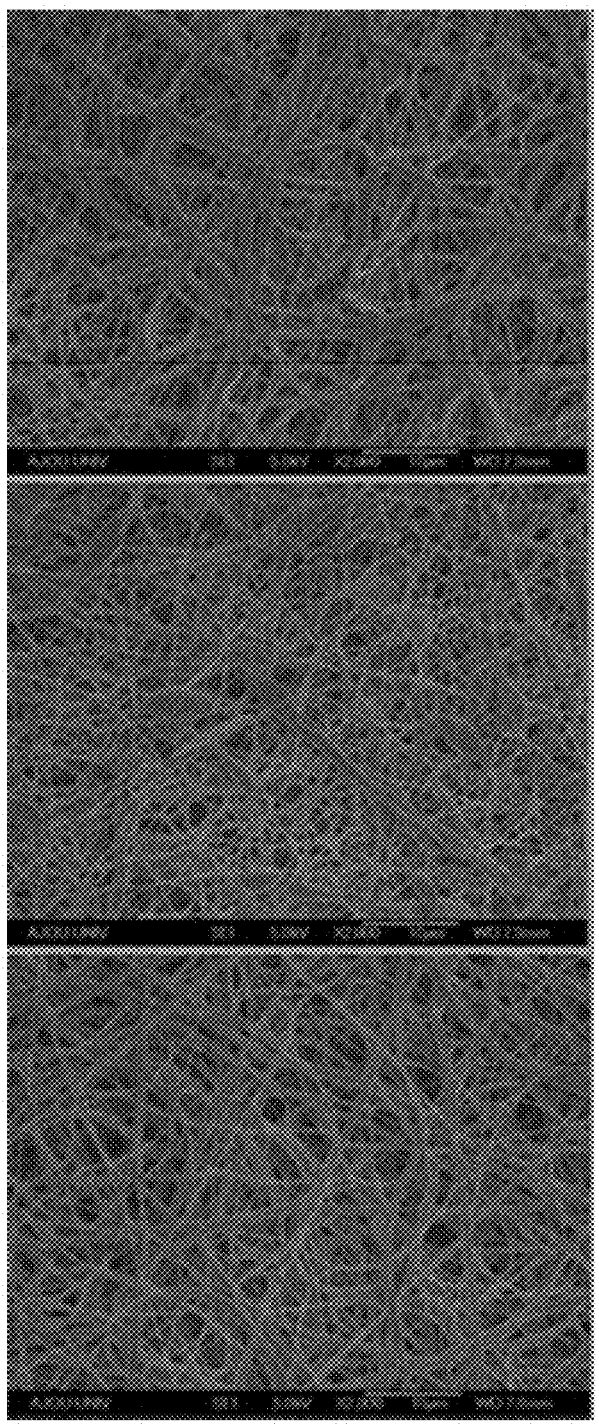
FIG. 1 illustrates results of observing a morphological structure or alteration of an electrospun nanofiber of solution of PCL in glacial acetic acid (GAA) with or without fucoidan.

After coating a PCL nanofiber with platinum, a morphological structure or variation of the electrospun PCL nanofiber was observed using a scanning electron microscope (SEM) (JSM-6700F, Japan). The results are illustrated in FIG. 1. Thickness and pore of the nanofiber mat were measured using an image analysis program (ImageJ. National Institutes of Health, Bethesda, Md., USA).

As shown in FIG. 1, PCL nanofiber blended with 1 mg/ml of fucoidan shows a more constant nanofiber shape than with 0.5 mg/ml of fucoidan. A homogeneous fucoidan-containing nanofiber could not be manufactured from 1.5 mg/ml or more of fucoidan by electrospinning since it was exhibited that 1.5 mg/ml or more of fucoidan was crystallized without being dissolved into a glacial acetic acid solution containing PCL.

It was shown that a nanofiber mat manufactured by electrospinning a PCL solution has more constant thickness and pore than a nanofiber mat which does not contain fucoidan.

<Experimental Example> Adhesion and Culture of Endothelial Cells in a Fucoidan/PCL Nanofiber Mat It was investigated if there was a difference between degree of adhesion of endothelial cells to a fucoidan/PCL nanofiber manufactured by Example of the present invention and degree of adhesion of the endothelial cells to a PCL nanofiber as Comparative Example.

EA.hy926 cells (ATCC, CRL-922) derived from human umbilical vein endothelial cells were used as the endothelial cells. The endothelial cells were cultured in a cell incubator maintaining 5% $CO_2$ using Dulbecco's modified eagle's medium (DMEM) culture medium including 10% FBS, 100 IU/ml penicillin, and 100 μg/ml streptomycin.

Endothelial cells ($1 \times 10^5$) were cultured in a state that nanofibers manufactured in the Example and Comparative Example were fixed to 8 well slides. Cells which had not been adhered to the nanofibers from 5 minutes to 24 hours after a culture were removed, and then the adhered cells in the mat were washed twice with culture medium. Adhered cells in the mat were then stained with 4',6-diamidino-2-phenylindole (DAPI) and fluorescein isothiocyanate (FITC)-conjugated phalloidin to confirm the number of cells adhered to the nanofibers. The results are illustrated in FIGS. 2A and 2B.

Figure 2A:
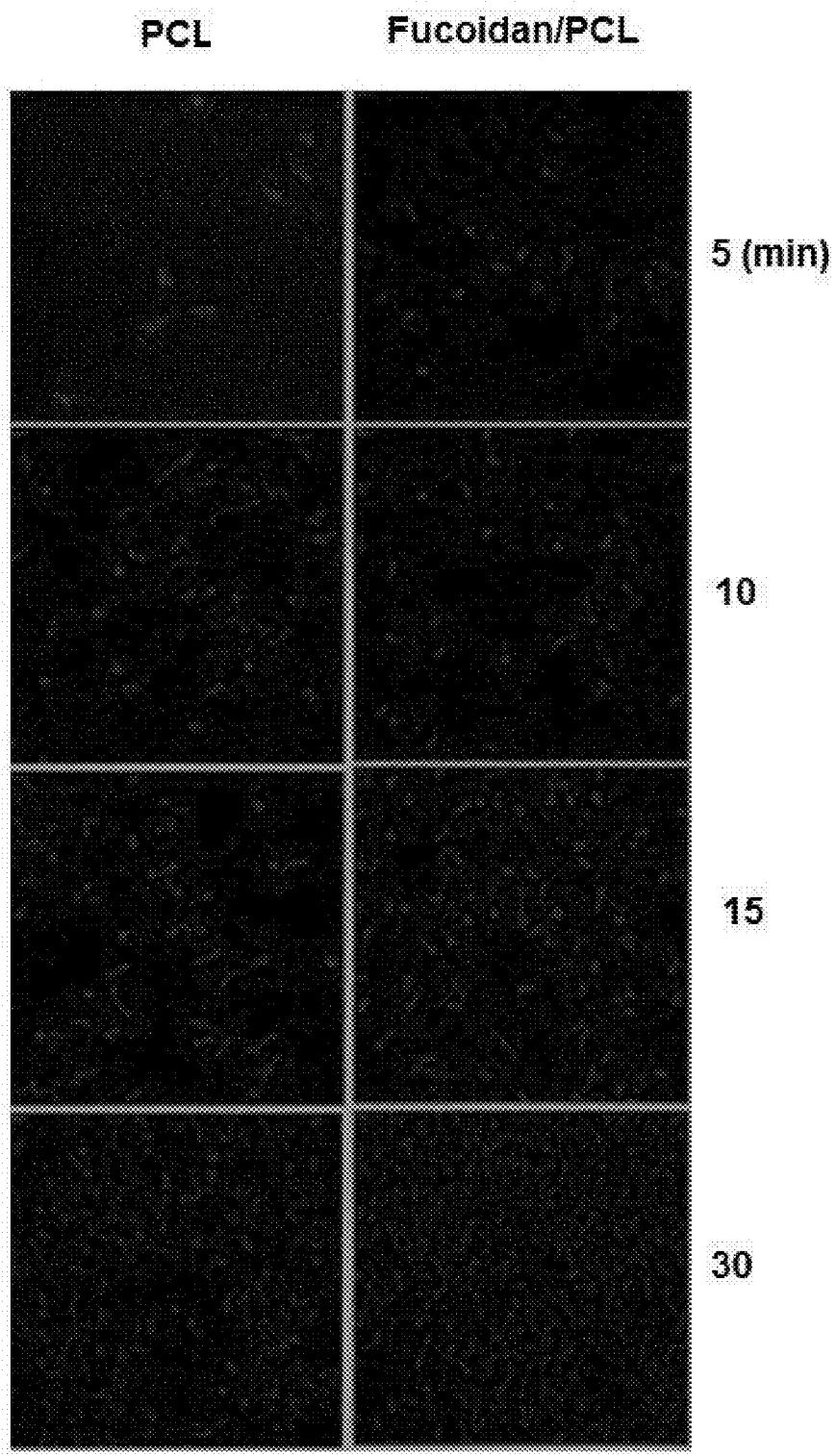

It is shown in FIGS. 2A and 2B that a remarkably large number of the endothelial cells are adhered to the entire surface of fucoidan/PCL nanofiber mat manufactured by Example of the present invention compared to the PCL nanofiber mat that is Comparative Example from one hour after cell culture.

<Experimental Example> Adhesion and Culture of Macrophages and Neutrophils in a Fucoidan/PCL Nanofiber Mat It was investigated if there was a difference between degree of adhesion of immune cells such as macrophages and neutrophils to a fucoidan/PCL nanofiber manufactured by Example of the present invention and degree of adhesion of the immune cells such as macrophages and neutrophils to a PCL nanofiber as Comparative Example.

Mouse peritoneal cavity-derived cells were used as the macrophages and neutrophils. The peritoneal neutrophils and the macrophages were isolated 5 hours and 3 days after injecting 2 ml of 3% thioglycollate into a mouse peritoneum, respectively, and $1 \times 10^5$ cells were cultured on a 96 well culture plate using a 200 μℓ RPMI-1640 culture medium (10% FBS, 100 IU/ml penicillin, and 100 μg/ml streptomycin).

After the macrophages which had been adhered to the plate for 2 days, were isolated from the plate and cultured again on the nanofibers, the cells that had not been adhered to the nanofibers after a predetermined time had passed were removed by washing of culture media. Then, the cells were washed twice with culture medium. Washed cells were then stained with DAPI and phalloidin to confirm the number of cells adhered to the nanofibers. The results are illustrated in FIG. 3A, FIG. 3B, and FIG. 4.

Figure 3A:
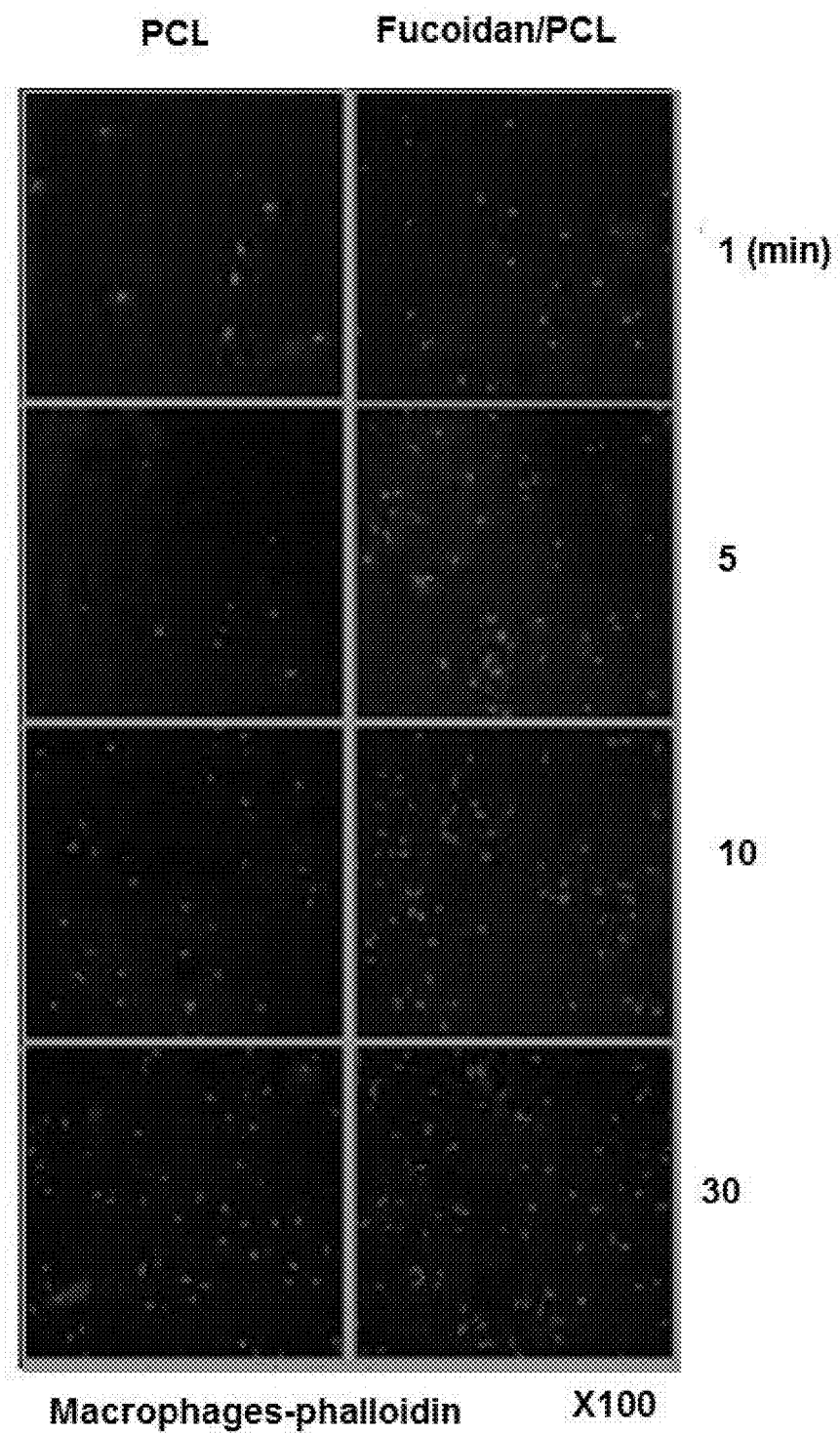
FIG. 3A and FIG. 3B illustrate results of experimenting degrees that mouse peritoneal macrophages (A) and neutrophils (B) are adhered to two types of nanofibers, i.e., the fucoidan/PCL nanofiber manufactured by Example of the present invention and the PCL nanofiber as Comparative Example according to the time.
Figure 3B:
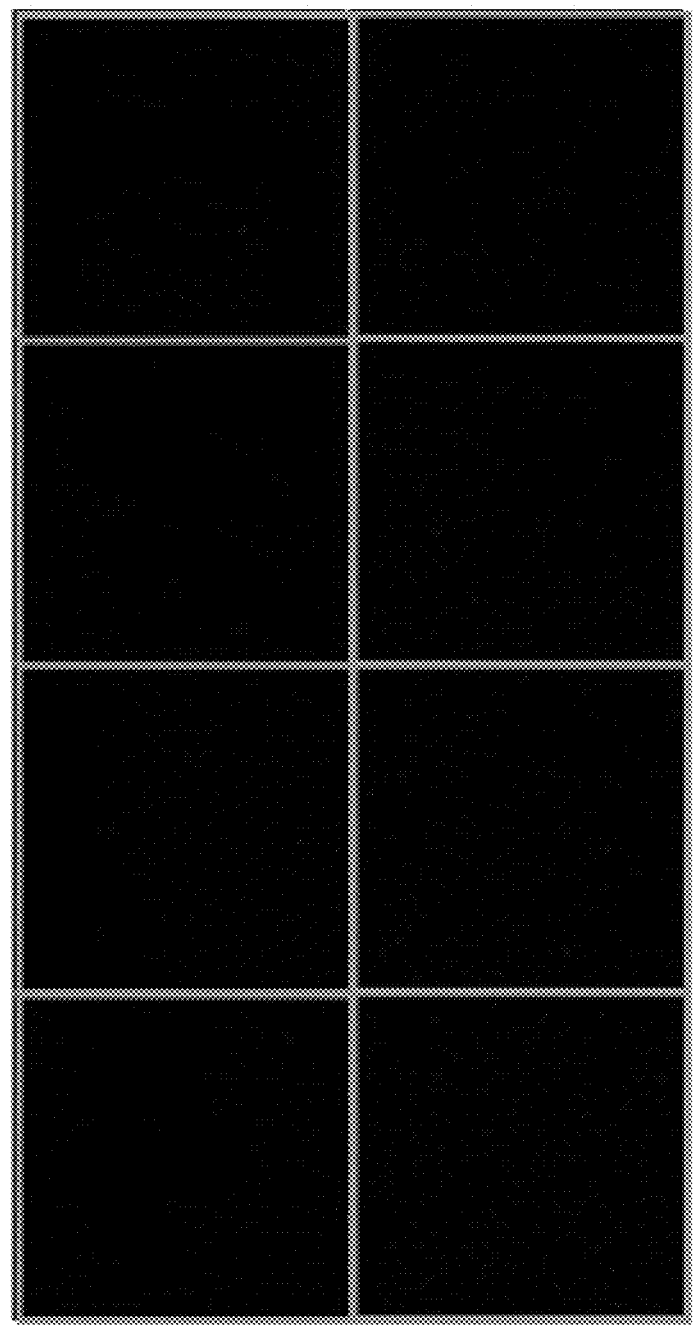
Figure 4:
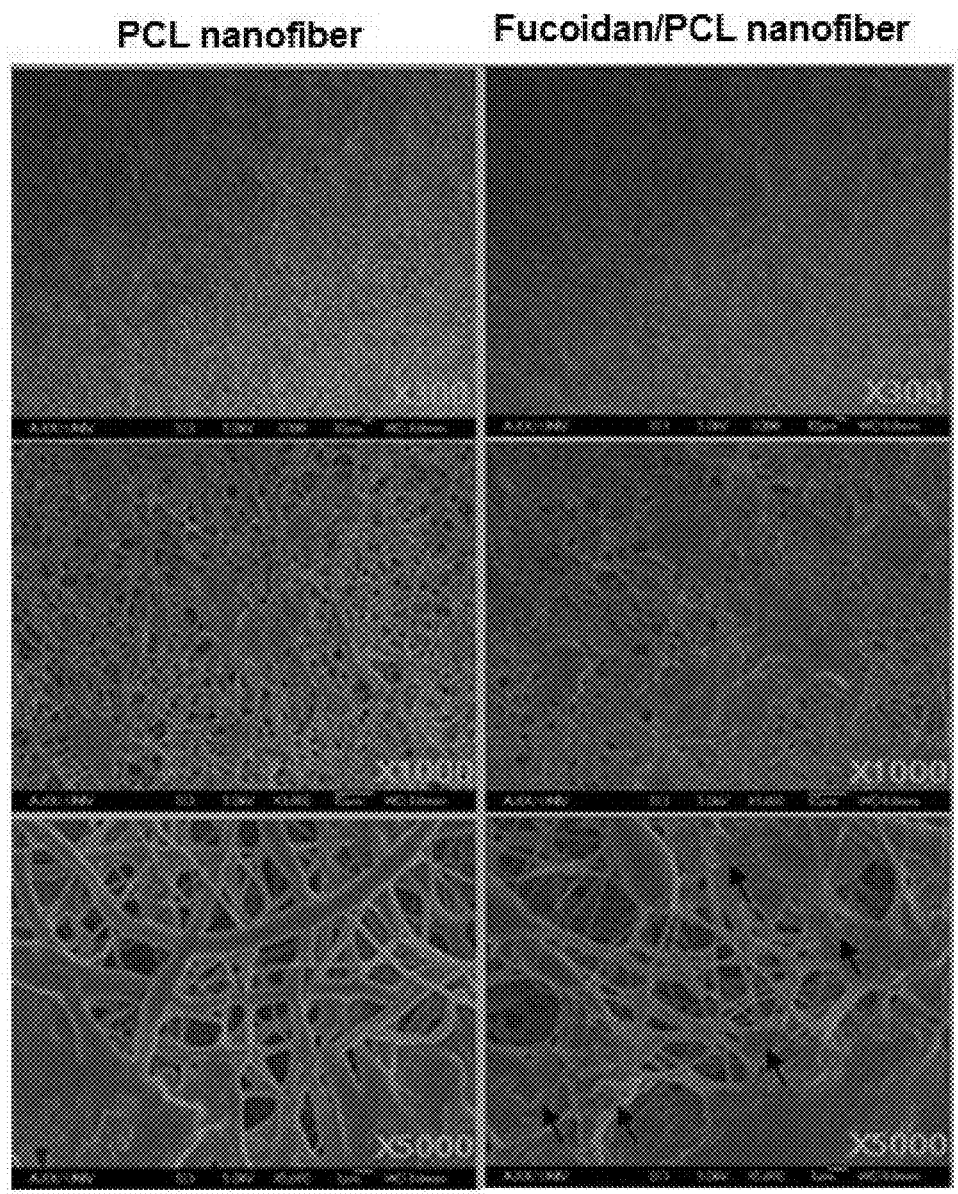
FIG. 4 illustrates results of experimenting degrees that macrophages are adhered to two types of nanofibers, i.e., the fucoidan/PCL nanofiber manufactured by Example of the present invention and the PCL nanofiber as Comparative Example according to the time.

It is shown in FIG. 3A, FIG. 3B, and FIG. 4 that macrophages and neutrophils are better adhered to the entire surface of the fucoidan/PCL nanofiber manufactured by Example of the present invention in a shorter period of time than the PCL nanofiber of Comparative Example after performing a top-seeding process.

<Experimental Example> Detecting Fucoidan within a Fucoidan/PCL Nanofiber

In order to detect whether fucoidan was contained in fucoidan/PCL or not, it was investigated if a nanofiber mat had been stained with methylene blue, thereby making the nanofibers react with fucoidan.

Figure 5A:
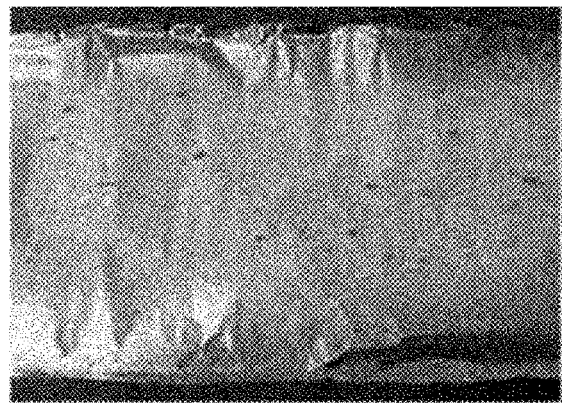
FIG. 5A and FIG. 5B are photographs of observing staining degrees of nanofibers obtained by treating a fucoidan/PCL nanofiber manufactured from fucoidan by a PCL nanofiber dissolved in chloroform as Comparative Example (FIG. 5A) and Example of the present invention (FIG. 5B) with alcian blue and washing the nanofibers treated with alcian blue.
Figure 5B:
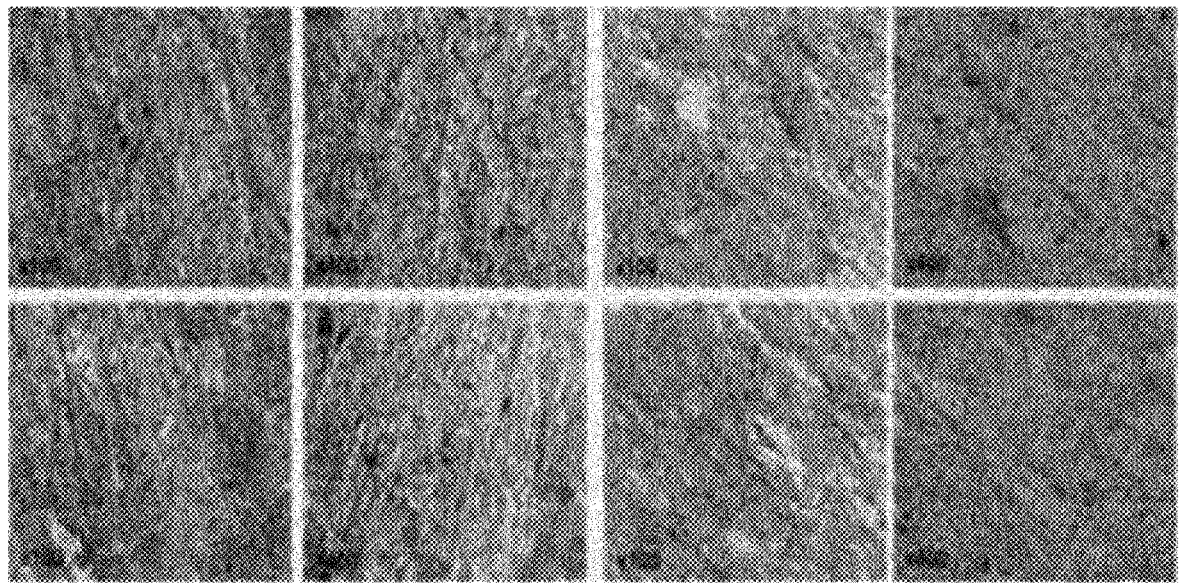

It is shown that a granular lump is formed on the nanofiber mat as in FIG. 5A since fucoidan is not completed dissolved in a nanofiber mat in which the mixture is electrospun after obtaining a mixture by mixing fucoidan with PCL dissolved in chloroform by Comparative Example of the present invention as illustrated in FIG. 5B.

Further, when the nanofiber of Comparative Example is stained with alcian blue, it can be seen as illustrated in FIG. 5B that the nanofiber is partially stained, and staining of only granular lump portions of the nanofiber are continued, but other portions of the nanofiber are decolorized after washing the stained nanofiber.

Figure 6A:
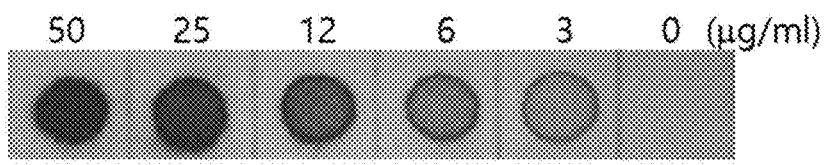
FIG. 6A is a drawing illustrating a staining degree obtained by methylene blue staining of a fucoidan solution with a different concentration dripped on filter paper.

<Experimental Example> Quantitatively and Qualitatively Detecting Fucoidan by Methylene Blue After drawing blanks with a size of 1×1 cm on a 110 mm filter paper, and dripping 2 µℓ of a fucoidan solution by concentration in each of the blanks, the fucoidan solution by concentration dripped in each of the blanks was dried in a drying oven to obtain a dried filter paper. A stained filter paper was obtained by staining the dried filter paper with the reagent at room temperature for 10 minutes after preparing a reagent by mixing 50 mM HCl and 0.1% methylene blue with a solution containing methanol, acetone and distilled water at a ratio of 6:4:15 (V/V). After washing the stained filter paper with distilled water three times, and the filter paper was decolorized with a decolorization reagent containing 5% acetic acid, 6% methanol, and 4% acetone at room temperature for 20 minutes to remove a staining solution which had not been coupled to fucoidan. It is shown as in FIG. 6A that a filter paper having a predetermined amount of fucoidan solution dripped thereon is stained with methylene blue.

Figure 6B:
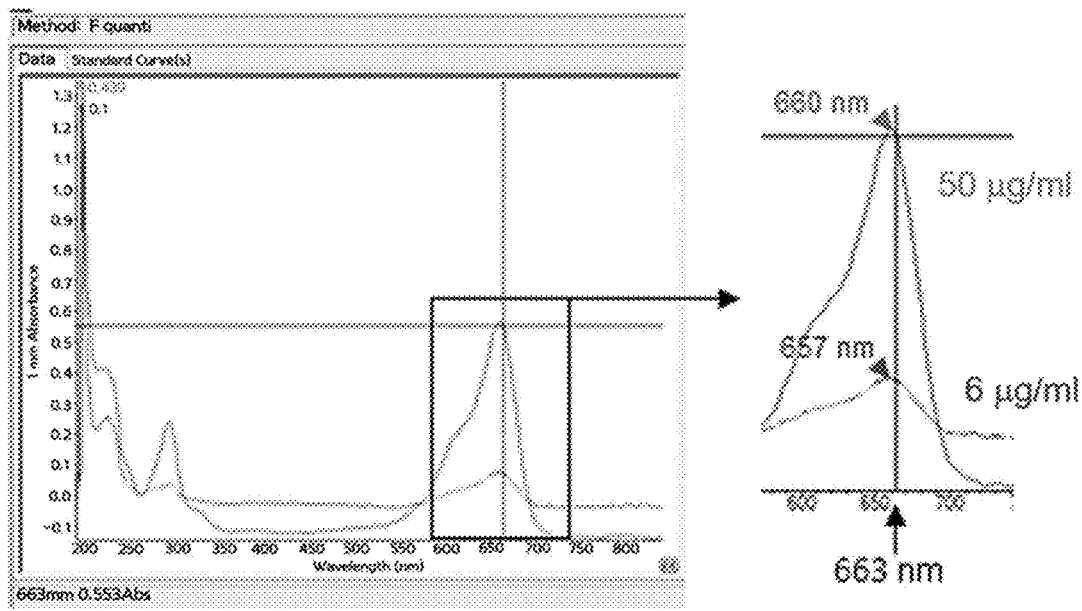
FIG. 6B is a drawing illustrating absorbance of methylene blue measured by a spectrophotometer to measure concentration of methylene blue.

Absorbance of a solution obtained by extracting stained methylene blue was measured to investigate whether or not staining degree of the filter paper is proportional to concentration of fucoidan. It is shown as in FIG. 6B that methylene blue represents a characteristic absorbance at 663 nm.

Figure 6C:
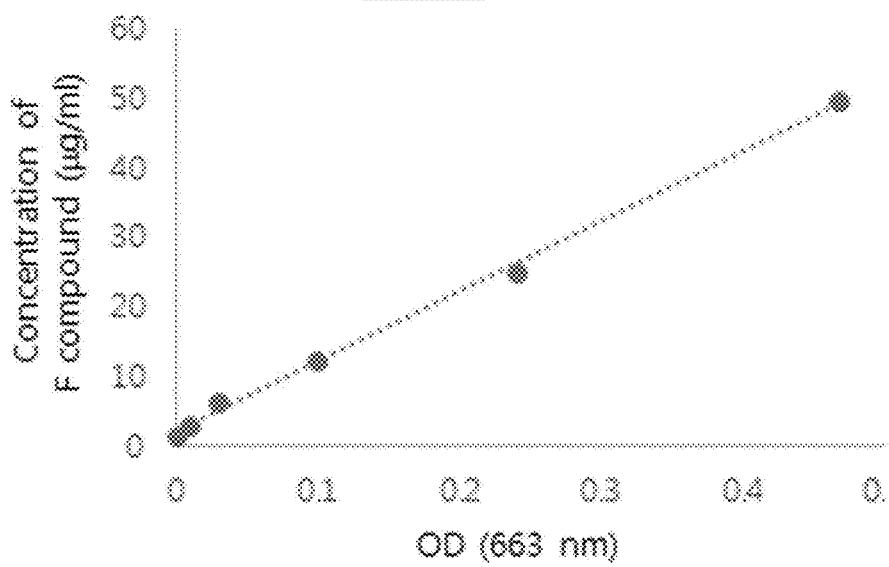
FIG. 6C is a drawing illustrating a standard curve of absorbance obtained by extracting and measuring methylene blue stained in the fucoidan dripped in FIG. 6A.

Absorbance of the solution was measured at 663 nm using a nanodrop spectrophotometer after putting the filter paper stained with methylene blue into an extraction solution composed of 70% ethanol and 2% sodium dodecyl sulfate and extracting methylene blue from the stained filter paper in a constant-temperature water bath at 50° C. for 15 minutes, thereby preparing a solution. Thus, a methylene blue dyeing method can be easily applied to detection of fucoidan contained in nanofiber since it is shown as in FIG. 6C that absorbance of methylene blue obtained by extracting a portion of the filter paper stained by dripping fucoidan on the filter paper is proportional to a dripping concentration of fucoidan.

Figure 7:
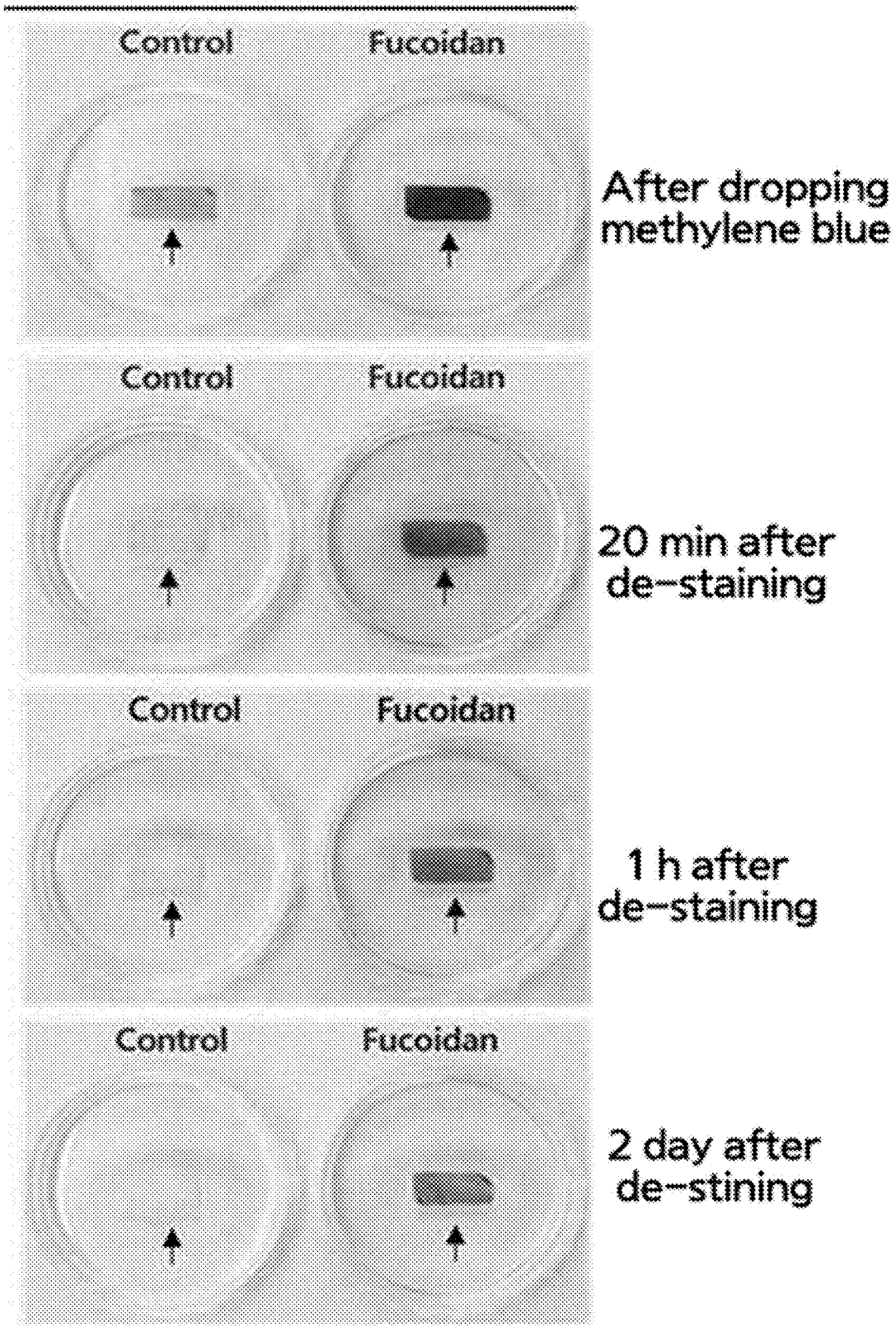
FIG. 7 is a drawing illustrating that fucoidan is contained in the fucoidan/PCL nanofiber manufactured by Example of the present invention using a methylene blue staining method.

<Experimental Example> Detecting Whether or not Fucoidan is Released from a Fucoidan/PCL Nanofiber In order to measure whether or not fucoidan within a fucoidan/PCL nanofiber is released by a de-staining solution, control PCL and fucoidan/PCL nanofiber mats were put into a decolorization reagent containing 5% acetic acid, 6% methanol and 4% acetone at room temperature for 20 minutes to remove a staining solution which had not been coupled to fucoidan. It is shown as in FIG. 7 that a fucoidan/PCL but not control PCL nanofiber mat was stained with methylene blue.

In addition, in order to measure whether or not fucoidan within a fucoidan/PCL nanofiber is released by a methylene blue extraction solution, a nanofiber mat was put into an extraction solution composed of 70% ethanol and 2% sodium dodecyl sulfate and making the nanofiber mat to react with the extraction solution in a constant-temperature water bath at 50° C. for a predetermined time, thereby producing a reaction product. And then, the reaction product was stained again with methylene blue to obtain a stained reaction product, and a decolorization process was secondly performed on the stained reaction product.

Figure 8A:
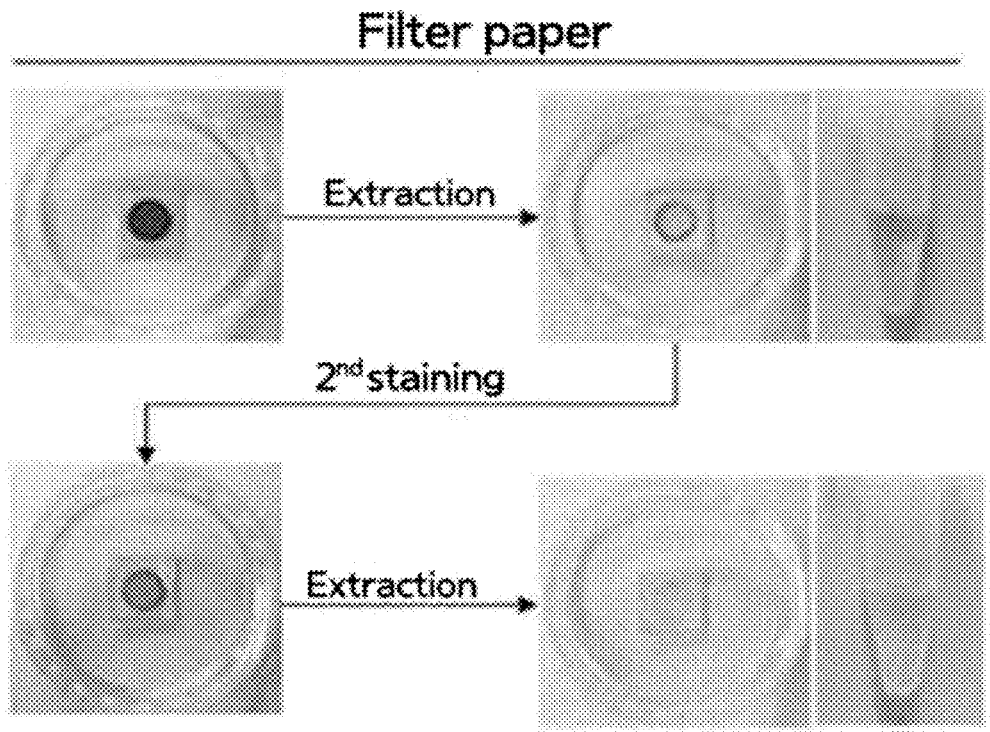
FIG. 8A and FIG. 8B are drawings illustrating that only the fucoidan/PCL nanofiber is stained when secondly staining the fucoidan/PCL nanofiber and fucoidan solution-dripped filter paper again after staining a fucoidan/PCL nanofiber and a fucoidan-dripped filter paper with methylene blue and treating the stained fucoidan/PCL nanofiber and fucoidan-dripped filter paper with an extract.
Figure 8B:
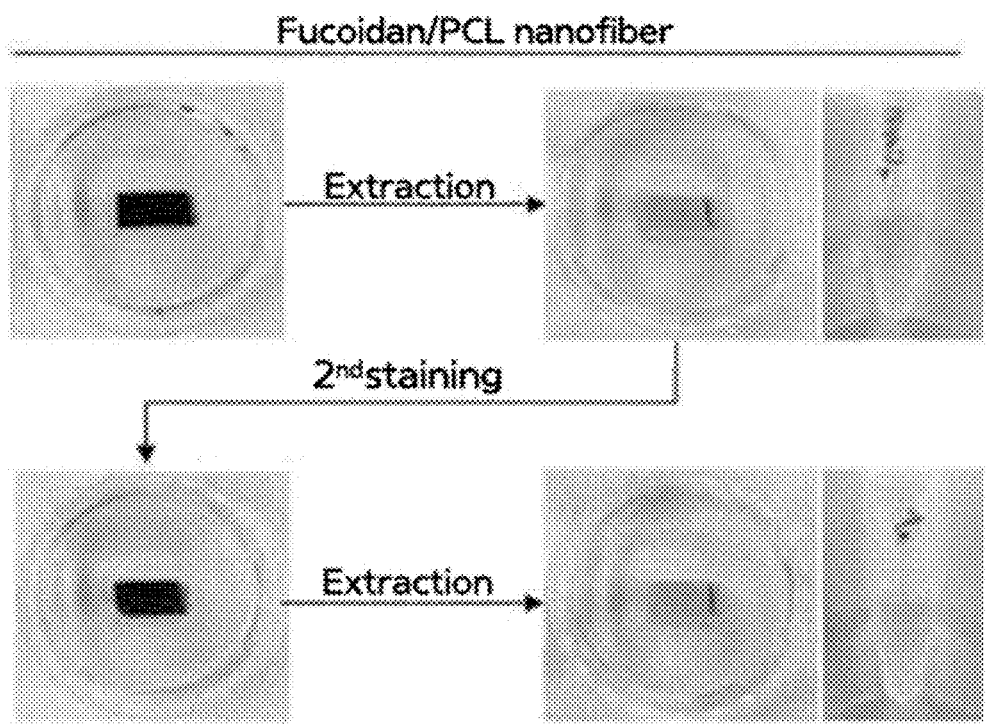

It is shown as in FIG. 8A and FIG. 8B that although a staining is not well observed when treating stained filter paper with extraction solution and performing a second staining process, a fucoidan-containing nanofiber is well stained to the same extent as in the case of performing a first staining process even when treating the fucoidan/PCL nanofiber mat with extraction solution and performing a second staining process. Therefore, it can be seen that fucoidan loaded on the nanofiber is not extracted, but is coupled to the nanofiber.

<Experimental Example> Measuring Production of Nitric Oxide (NO) in Cells Cultured in a Fucoidan/PCL Nanofiber Mat It has not been clearly known whether fucoidan binds to the cells, and then passes through a specific receptor or non-specifically enters the cells when activation occurs in fucoidan-treated cells. Therefore, degrees of NO production were measured and compared as effects of fucoidan between when cells were treated with fucoidan when fucoidan was coupled to.

Production of NO as an extent of color developed using a Griess reagent (G4410, Sigma), was measured at an absorbance of 540 nm using a spectrophotometer (UVT 06856, Molecular Devices Corporation). Endothelial cells and macrophages ($1\times10^5$) were seeded onto a 8 well plate and treated with 100 µg/ml of fucoidan and/or 1 µg/ml of lipopolysaccharide (LPS), and then cultured for two days in the case of second-dimensional culture state. These cells ($1\times10^5$) were also seeded onto a PCL nanofiber mat and a fucoidan/PCL nanofiber mat and cultured with or without LPS for two days. Absorbance of the reaction product were measured by adding a 1×Griess reagent at a ratio of 1:1 to a culture medium isolated after a cell culture, and reacting the 1×Griess reagent with the culture medium for 15 minutes to obtain a reaction product.

Figure 9A:
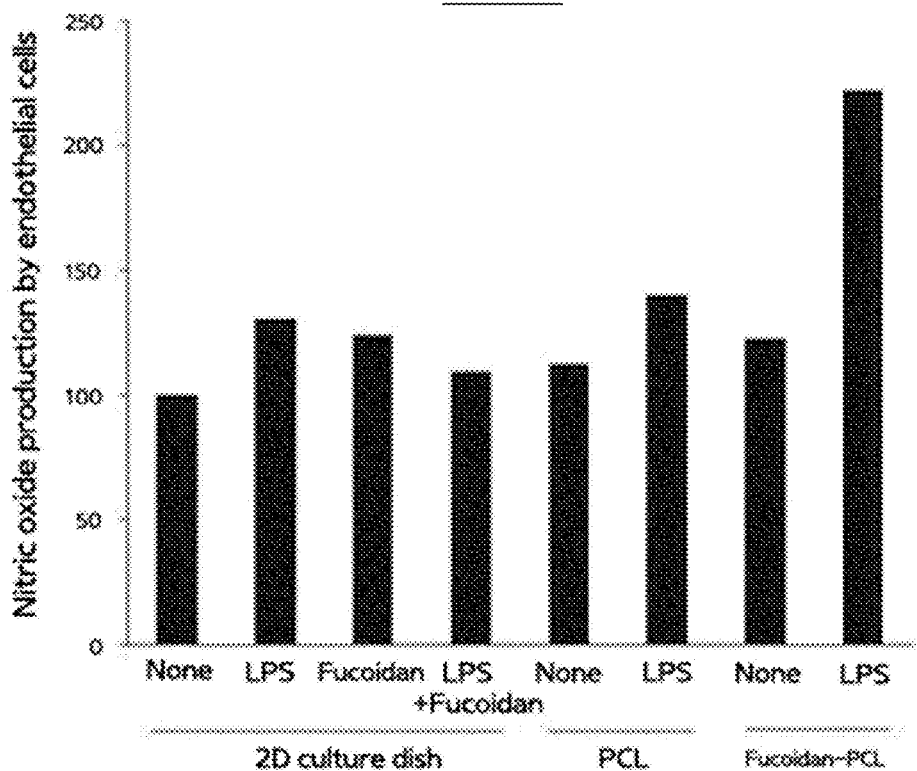
FIG. 9A and FIG. 9B illustrate measurement comparison results obtained by measuring and comparing production amounts of nitric oxide (NO) produced while culturing endothelial cells and macrophages in a two-dimensional culture plate, a PCL nanofiber mat, and a fucoidan/PCL nanofiber mat.
Figure 9B:
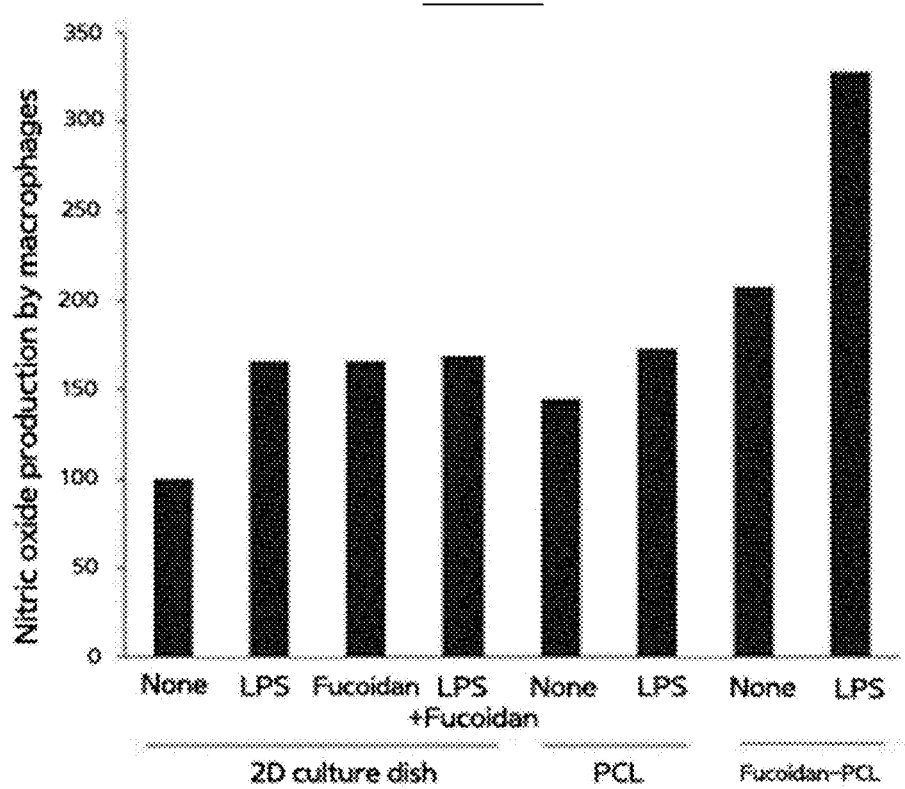

It is shown as in FIG. 9A and FIG. 9B that although production of NO was increased when treating endothelial cells or macrophages with LPS or fucoidan in a two-dimensional culture without using a nanostructure, synergistic effects were not exhibited when treating the endothelial cells or macrophages with both reagents of LPS and fucoidan at the same time.

On the contrary, production of NO was greatly increased although only LPS was added to cells cultured in a fucoidan/PCL nanofiber mat manufactured by Example of the present invention. Production of NO was not greatly increased in cells cultured in a PCL nanofiber mat differently from the cells cultured in the fucoidan/PCL nanofiber mat even after treating the cells cultured in the PCL nanofiber mat with LPS. Accordingly, this suggests that fucoidan contained in nanofibers is coupled to the cells such that the fucoidan contained in the nanofibers has a great effect on cell activity.

A method of manufacturing a PCL nanostructure with improved cell adhesive ability containing fucoidan according to the present invention comprises dissolving fucoidan in glacial acetic acid as a solvent to obtain fucoidan-glacial acetic acid solution and manufacturing a nanostructure from the fucoidan-glacial acetic acid solution by an electrospinning method. A PCL nanofiber structure with improved cell adhesive ability containing fucoidan manufactured the above-described method according to the present invention has characteristics of preventing fucoidan from being released from nanofibers by uniformly distributing fucoidan in the PCL nanostructure, thereby exhibiting an effect capable of controlling cell activity while culturing adhered cells by facilitating adhesion of various types of cells. Therefore, industrial applicabilities of a method of manufacturing a PCL nanostructure with improved cell adhesive ability containing fucoidan according to the present invention, and a PCL nanostructure with improved cell adhesive ability containing fucoidan manufactured thereby are acknowledged.

What is claimed is:

1. A method of manufacturing a polycaprolactone nanostructure with improved cell adhesive ability containing fucoidan, the method comprising the steps of:
   dissolving fucoidan in distilled water to obtain fucoidan-dissolved distilled water, and mixing the fucoidan-dissolved distilled water with a glacial acetic acid solution to obtain a fucoidan-glacial acetic acid solution;
   dissolving polycaprolactone in the fucoidan-glacial acetic acid solution to obtain a solution;
   stirring the solution at a temperature of 35 to 40° C. for 12 hours to obtain a resulting solution; and
   manufacturing a nanostructure from the solution by an electrospinning method,
   wherein, the fucoidan-glacial acetic acid solution obtained by the step of mixing the fucoidan-dissolved distilled water with a glacial acetic acid solution comprises 0.5 to 1 mg/ml of fucoidan.

2. The method of claim 1, wherein the step of manufacturing a nanostructure from the solution by an electrospinning method comprises manufacturing a nanostructure from the solution by an electrospinning method at a voltage of 8 to 10 KV and a spinning speed of 8 to 10 µg/min.

3. A polycaprolactone nanostructure with improved cell adhesive ability containing fucoidan manufactured according to the method of claim 1.

4. A polycaprolactone nanostructure with improved cell adhesive ability containing fucoidan manufactured according to the method of claim 2.

* * * * *